(12) United States Patent
Nelson (10) Patent No.: US 11,660,466 B2
(45) Date of Patent: May 30, 2023

(54) SKIN THERAPY DEVICE

(71) Applicant: LED Technologies Inc., Largo, FL (US)

(72) Inventor: Lloyd Nelson, Largo, FL (US)

(*) Notice: Subject to any disclaimer, the term of this patent is extended or adjusted under 35 U.S.C. 154(b) by 0 days.

(21) Appl. No.: 17/465,910

(22) Filed: Sep. 3, 2021

(65) Prior Publication Data

US 2023/0072776 A1     Mar. 9, 2023

(51) Int. Cl.
| | | |
|---|---|---|
| *A61N 5/06* | (2006.01) | |
| *F21V 15/01* | (2006.01) | |
| *A61H 23/02* | (2006.01) | |
| *F21Y 115/10* | (2016.01) | |
| *F21Y 113/10* | (2016.01) | |

(52) U.S. Cl.
CPC ....... *A61N 5/0616* (2013.01); *A61H 23/0263* (2013.01); *F21V 15/01* (2013.01); *A61H 2201/10* (2013.01); *A61N 2005/0652* (2013.01); *A61N 2005/0659* (2013.01); *A61N 2005/0663* (2013.01); *F21Y 2113/10* (2016.08); *F21Y 2115/10* (2016.08)

(58) Field of Classification Search
CPC .......... A61N 5/0616; A61N 2005/0652; A61N 2005/0659; A61N 2005/0663; A61H 23/0263; A61H 2201/10; F21V 15/01; F21Y 2113/10; F21Y 2115/10
See application file for complete search history.

(56) References Cited

U.S. PATENT DOCUMENTS

| | | | |
|---|---|---|---|
| 7,386,906 B2 * | 6/2008 | Roth ...................... | A46B 13/06 15/97.1 |
| 8,500,754 B2 * | 8/2013 | Hull, Jr. ............. | A61B 17/3205 606/131 |
| 9,138,257 B2 * | 9/2015 | Revivo .................. | A61H 7/005 |
| 9,579,250 B2 * | 2/2017 | Nichols ............... | A46B 13/008 |
| 10,307,330 B1 | 6/2019 | Sedic | |
| 10,531,729 B1 * | 1/2020 | Liu .......................... | A46B 5/02 |
| 10,966,514 B2 * | 4/2021 | Goldberg ............. | A46B 13/008 |
| 2007/0038206 A1 * | 2/2007 | Altshuler ........... | A46B 15/0036 606/20 |
| 2009/0177125 A1 * | 7/2009 | Pilcher ............... | A46B 15/0034 15/4 |
| 2013/0158547 A1 * | 6/2013 | David .................. | A61N 5/0616 606/41 |
| 2014/0013525 A1 * | 1/2014 | Zhou ...................... | A46B 13/02 15/22.1 |
| 2014/0135798 A1 * | 5/2014 | David .................. | A61N 5/0624 606/131 |
| 2014/0202493 A1 * | 7/2014 | Zelickson ............ | A61N 5/0616 134/6 |

(Continued)

*Primary Examiner* — Tsion Tumebo
(74) *Attorney, Agent, or Firm* — Larson & Larson; Justin P. Miller; Frank Liebenow (57) ABSTRACT

The skin therapy device combines the mechanical stimulation and cleansing in the form of vibration with optical stimulation from LEDs. The device combines these two elements without sacrificing the effectiveness of either the mechanical cleansing/stimulation or optical stimulation by passing the light through the mechanical elements that are in contact with the skin. The light from the LEDs does not pass around the mechanical elements, such as around opaque brush fibers, but passes through the mechanical elements.

15 Claims, 12 Drawing Sheets

(56) References Cited

U.S. PATENT DOCUMENTS

| | | | | |
|---|---|---|---|---|
| 2016/0183671 A1* | 6/2016 | Skidmore | ............... | A61H 7/005 |
| | | | | 173/162.2 |
| 2017/0332850 A1* | 11/2017 | Powell | ................. | A46B 5/0095 |
| 2017/0367543 A1* | 12/2017 | Straka | .................... | A61H 7/005 |
| 2018/0178032 A1* | 6/2018 | Pilcher | ................ | A61N 5/0616 |
| 2018/0184794 A1* | 7/2018 | Matsushita | ............ | A46B 13/02 |
| 2019/0262607 A1* | 8/2019 | Nichols | .............. | A46B 15/0034 |
| 2020/0179220 A1* | 6/2020 | Jablow | ..................... | A61H 1/00 |
| 2020/0352306 A1* | 11/2020 | Um | ........................... | A61L 2/26 |
| 2021/0154093 A1* | 5/2021 | Boone, III | ........... | A61H 9/0057 |
| 2021/0339040 A1* | 11/2021 | Truong | ................ | A61N 5/0616 |
| 2022/0095782 A1* | 3/2022 | Kosecoff | .............. | A46B 11/002 |

\* cited by examiner

SKIN THERAPY DEVICE

FIELD

This invention relates to the field of skin therapy and more particularly to a device that stimulates the skin by applying light while mechanically cleansing or stimulating the skin.

BACKGROUND

As the largest organ of the body, and the organ that is most in contact with the harsh outside world, skin is subject to significant abuse.

To help the skin address this abuse, there are therapies in the form of mechanical cleansing/stimulation and light stimulation.

But mechanical cleansing or simulating, and light stimulation in the form of shining certain frequencies of light onto the skin, are time consuming to apply individually.

What is needed is a device that will allow a user to simultaneously apply mechanical stimulation and light stimulation, while maintaining the effectiveness of both.

SUMMARY

The skin therapy device combines mechanical cleansing and stimulation in the form of vibration with optical stimulation from LEDs.

The device combines these two elements without sacrificing the effectiveness of either the mechanical cleansing/stimulation or optical stimulation by passing the light through the mechanical elements that are in contact with the skin.

The light from the LEDs does not pass around the mechanical elements, such as around opaque brush fibers, but passes through the mechanical elements.

This is an important distinction because by passing through, the field of light is uninterrupted. This is distinguishable from prior art with opaque brush fibers—such as nylon fibers—or other mechanical elements that block regions of light, creating a speckled, or inconsistent, field of light. The result of such a varied light field is inconsistent optical stimulation, creating inconsistent skin therapy, and may result in variations in skin color or areas of irritation due to light concentration.

By using a protective cover around the LEDs, they are protected from mechanical damage and intrusion of liquids. The protective cover is transparent to the therapeutic light.

A removable silicone head attaches to the protective cover, the removable silicone head also transparent to therapeutic light.

In the preferred embodiment vibration is created by an electric motor with a weight affixed to its output shaft. The weight is off-balance, creating vibration as the motor spins the weight.

The skin therapy device can be many shapes. The preferred embodiment is nearly spherical, meant for being held in the palm. But alternative embodiments include longer wand-shaped variations. Such larger sizes create additional internal space for components, such as larger batteries.

The power source of the skin therapy device varies depending on the intended user. A rechargeable source, such as a lithium-ion or nickel-metal hydride battery, is ideal for more expensive models, with less expensive models leaving the user to insert disposable batteries.

The therapeutic light from the LEDs is of one or more frequencies chosen to address specific skin conditions.

For example, acne is treated using a combination of two frequencies: 415 nm blue light and 630 nm red light.

An anti-aging skin treatment uses a combination of three frequencies: 605 nm amber light, 630 nm red light, 660 nm deep red light, and 880 nm infrared light.

Multiple LED sets are used to emit the multiple frequencies of light. For example, a first set of LEDs for 415 nm light, and a second set of LEDs for 630 nm light.

The LEDs are mounted to a circuit board, which sits inside the protective cover. A locking plate sits within the protective cover, holding the circuit board in place. The locking plate removably interfaces with the protective cover, preferably using tabs to lock into slots within the protective cover.

The protective cover also interfaces with the body of the skin therapy device via tabs on the outer shell of the body. In the preferred embodiment, each slot of the protective cover interfaces with both a tab of the locking plate and a tab of the outer shell of the body.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Reference will now be made in detail to the presently preferred embodiments of the invention, examples of which are illustrated in the accompanying drawings. Throughout the following detailed description, the same reference numerals refer to the same elements in all figures.

Figure 1:
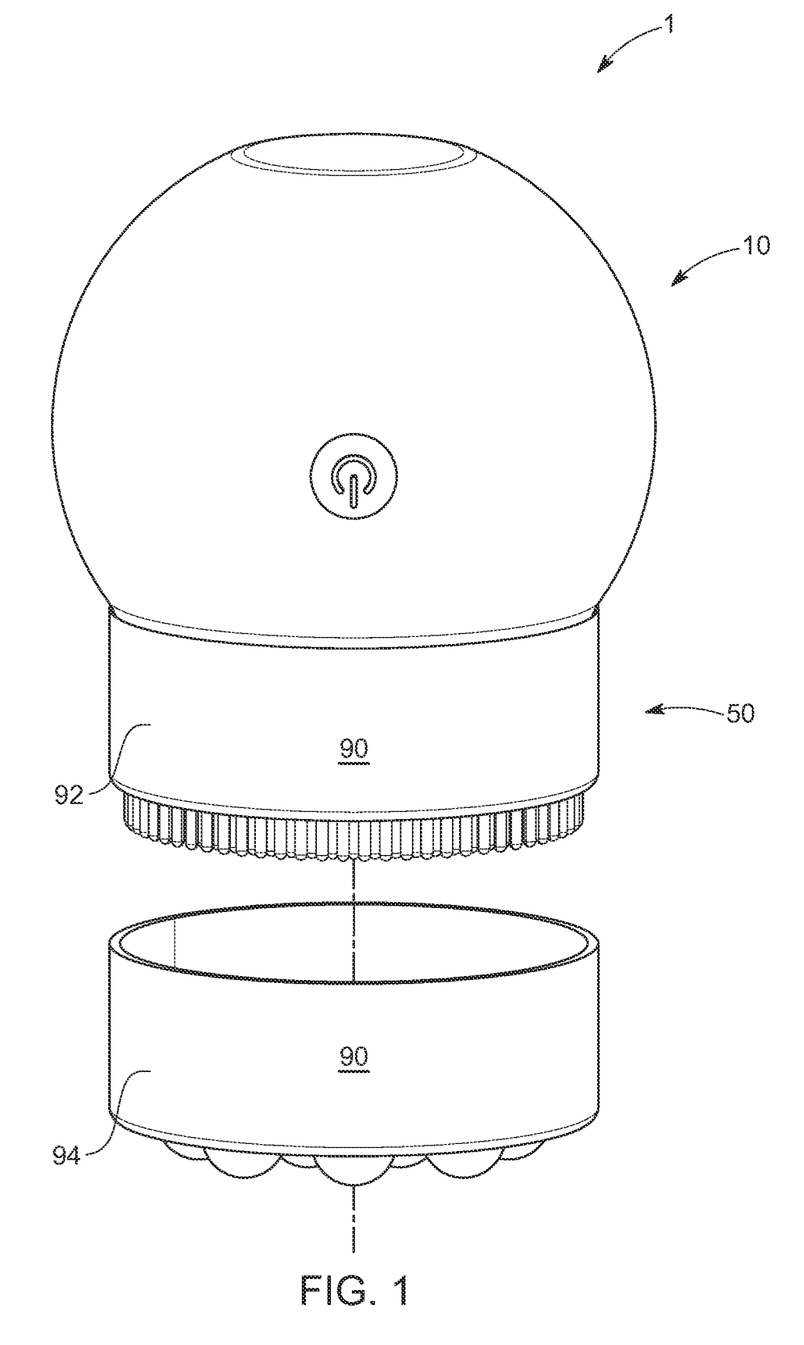
FIG. 1 illustrates a first isometric view of the skin therapy device.

Referring to FIG. 1, a first isometric view of the skin therapy device is shown.

The skin therapy device 1 includes primary components of body 10 and silicone head 90. The silicone head 90 is shown in two embodiments cleansing head 92 and massaging head 94. Both types of silicone head 90 affix to the protective cover 80 (see FIG. 2), differing primarily in the type and shape of protrusions. The cleansing head 92 includes many smaller protrusions for a scrubbing action, the massaging head 94 includes fewer, larger protrusions for a gentler interaction with the skin.

The silicone head 90 is preferably formed from a flexible material that is stretched, or rolled, over the protective cover 80.

Figure 2:
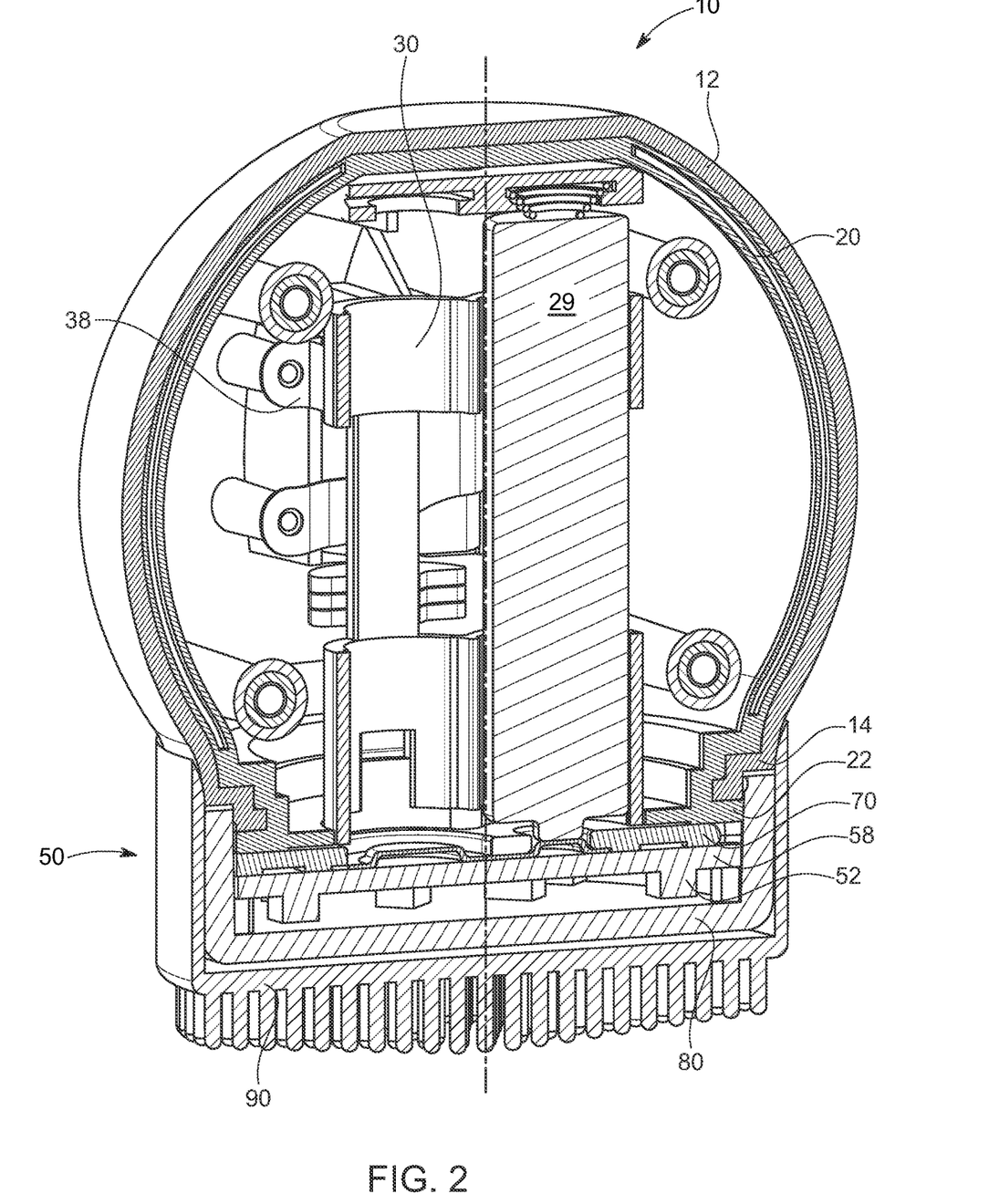
FIG. 2 illustrates a first cross-sectional view of the skin therapy device.
Figure 3:
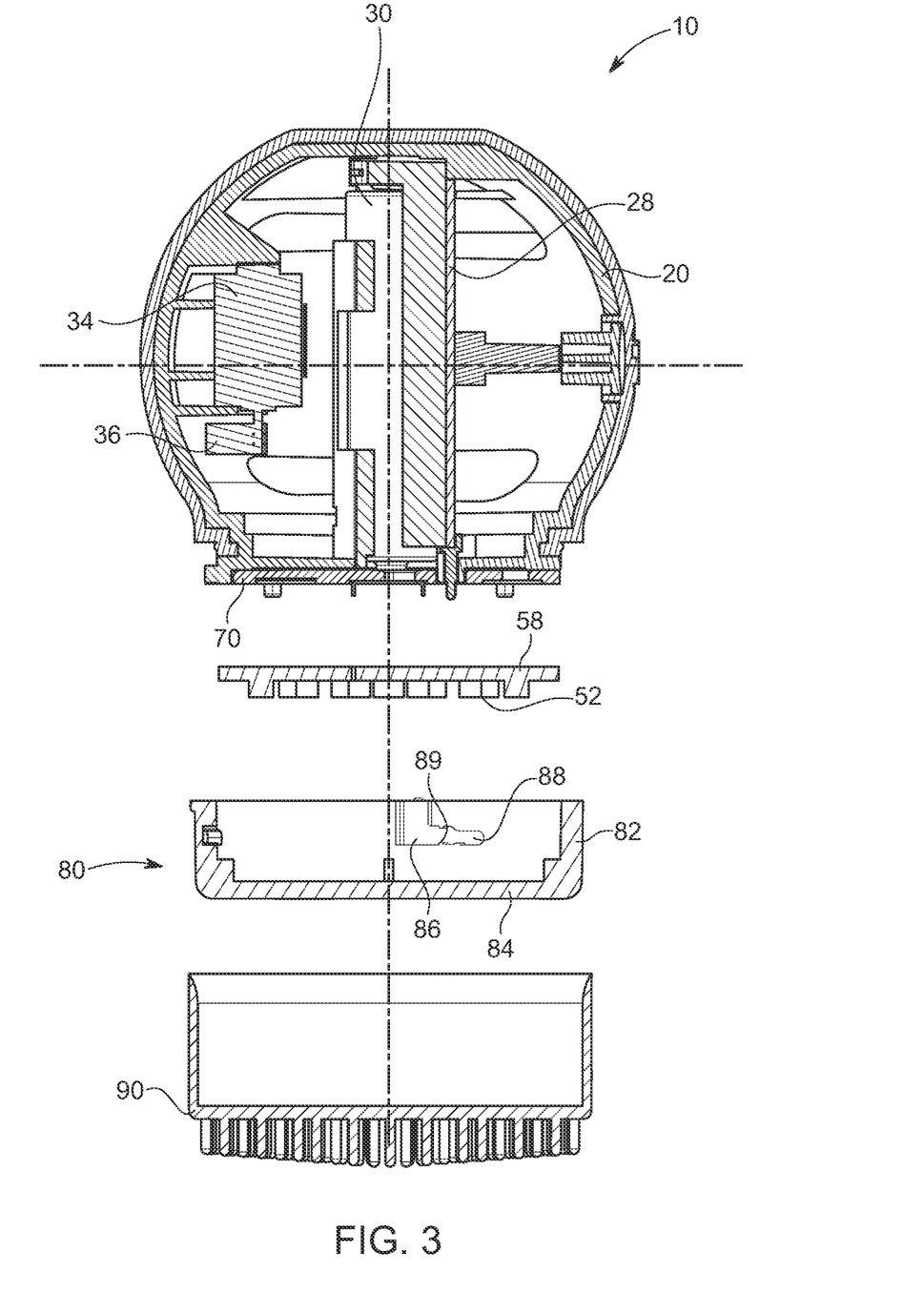
FIG. 3 illustrates a second, partially-exploded, cross-sectional view of the skin therapy device.

Referring to FIGS. 2 and 3, a first cross-sectional view, and a second, partially-exploded, cross-sectional view, of the skin therapy device are shown.

The body 10 of the skin therapy device 1 is formed from an outer skin 12 and an inner shell 20. In the preferred embodiment, the outer skin 12 is a softer material, such as silicone, and the inner shell 20 is a more rigid, structural material such as metal or stiff plastic.

The outer skin 12 includes a locking rim 14 that fits into a locking ledge 22 of the inner shell, holding the layers together.

Within the body is one or more battery 29, held in place by battery support 30.

A motor bracket 38 is affixed to the inner shell 20, holding motor 34 that spins an unbalanced weight 36 to create vibration. The vibration is passed through the inner shell 20, to the locking plate 70, to the protective cover 80, and finally to the silicone head 90.

A locking plate 70 joins the protective cover 80 to the body 10, holding the LED circuit board 58 within the protective cover 80 and against the inner shell 20.

The LED emitters 52 are placed beneath the LED circuit board 58 where they can emit light through the protective cover 80 and the silicone head 90.

The protective cover 80 includes a locking slot 86 with a first locking section 88 and a second locking section 89. The locking plate 70 interfaces with the locking slot 86, resting at the first locking section 88. The inner shell 20 also interfaces with the locking slot 86, resting at the second locking section 89. Thus, each locking slot 86 connects the locking plate 70 to the inner shell 20, holding the skin therapy device 1 together.

The protective cover 80 is formed from wall 82 and face 84.

Figure 4:
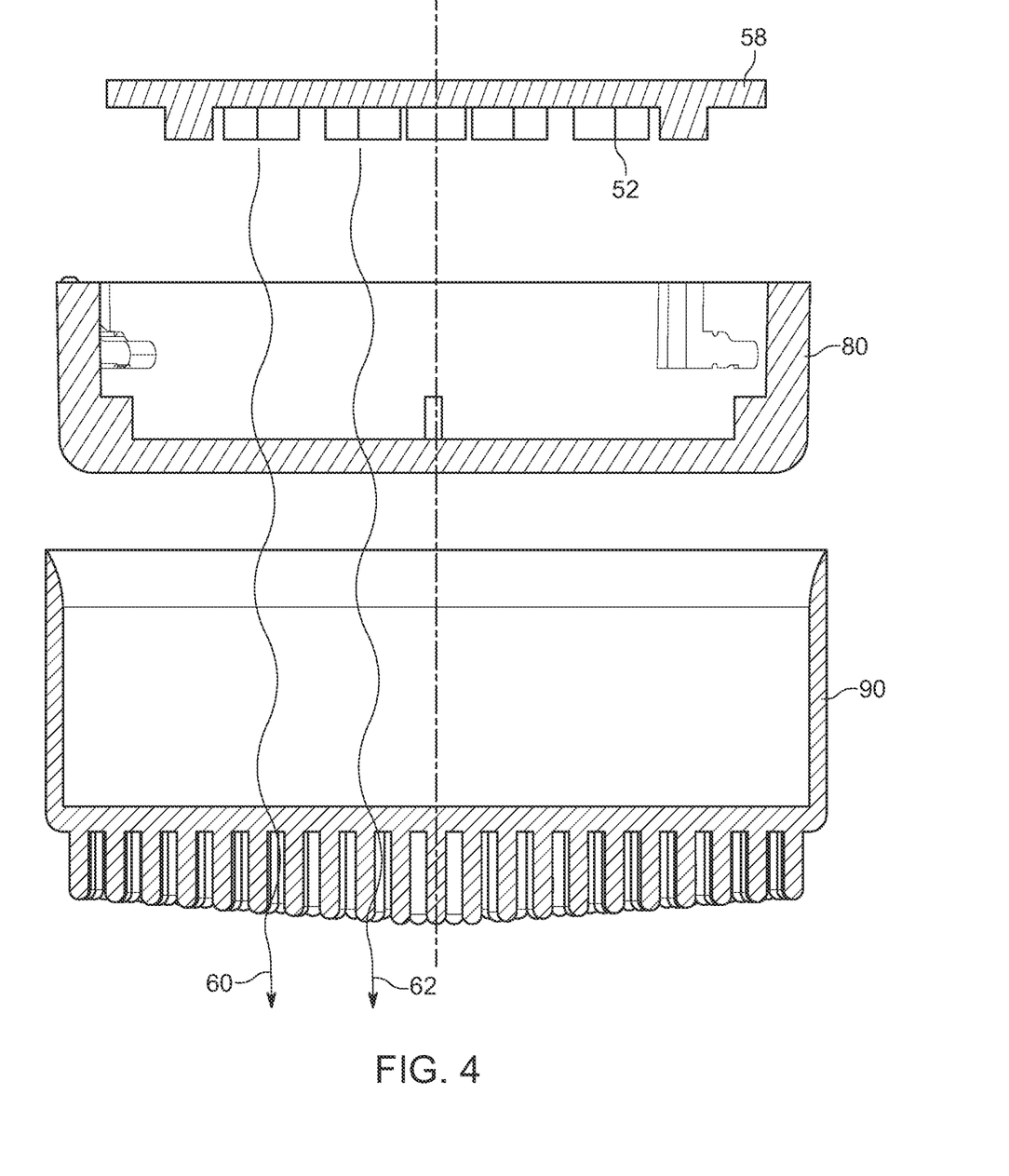
FIG. 4 illustrates an exploded view of the base and head, with LEDs, of the skin therapy device.

Referring to FIG. 4, an exploded view of the base and head, with LEDs, of the skin therapy device is shown.

The skin therapy device 1 simultaneously emits therapeutic light, while also massaging or abrading the skin.

This is accomplished by allowing light to shine through the lower elements of the device, while protecting the electronics from contact with water, skin oils, and so forth.

The LED circuit board 58 includes LED emitters 52 that emit light at one or more wavelengths. For example, light at wavelength one 60 and light at wavelength two 62.

The light 60/62 passes through the optically transparent protective cover 80 and through the optically transparent silicone head 90, reaching the user's skin below.

In the preferred embodiment, there are no holes in the protective cover 80 or silicone head 90 to allow light 60/62 to pass. Rather, the LED emitters 52 are physically isolated from the user's skin below, the light passing through to reach the skin.

Figure 5:
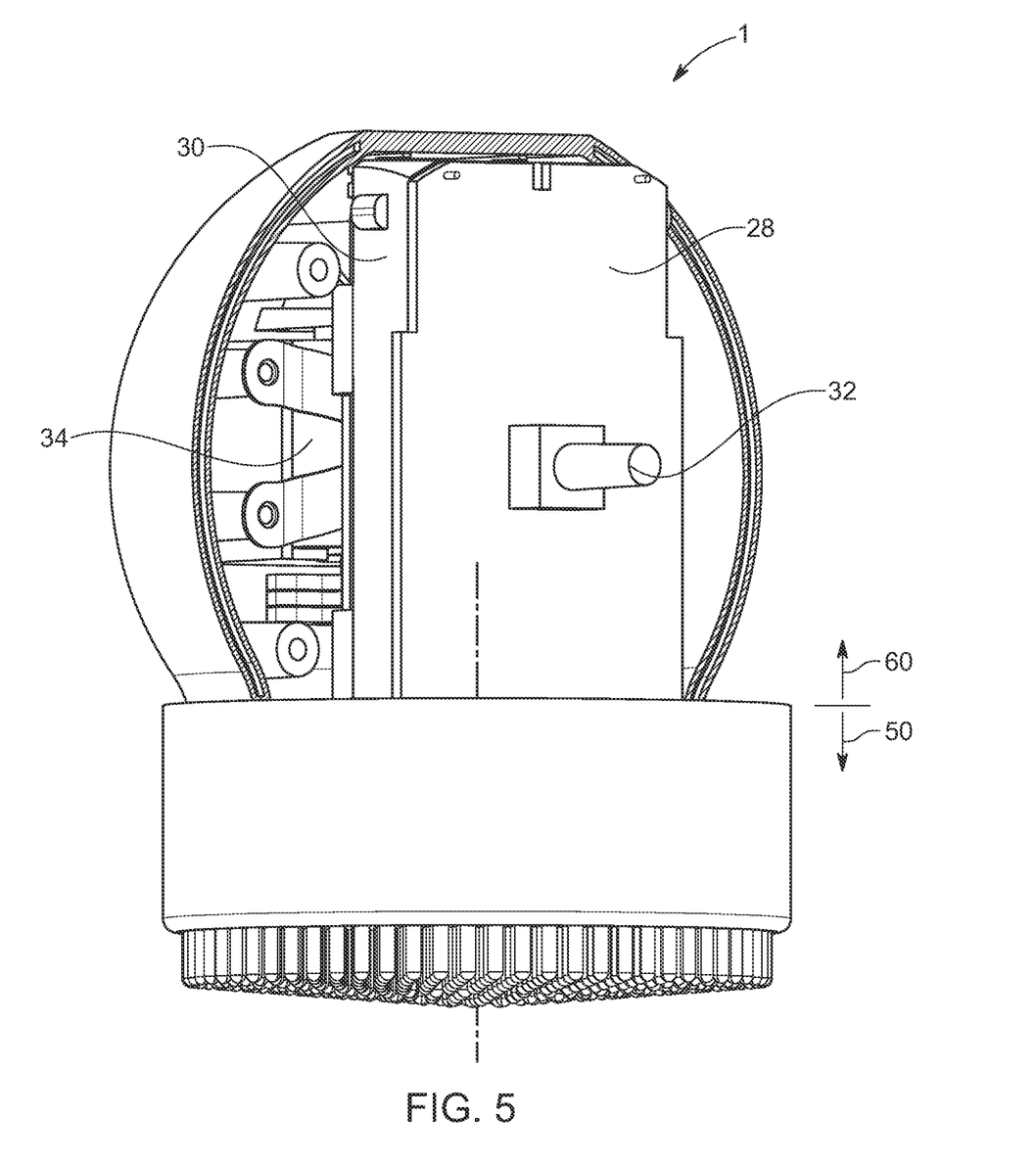
FIG. 5 illustrates a first cutaway view of the skin therapy device.
Figure 6:
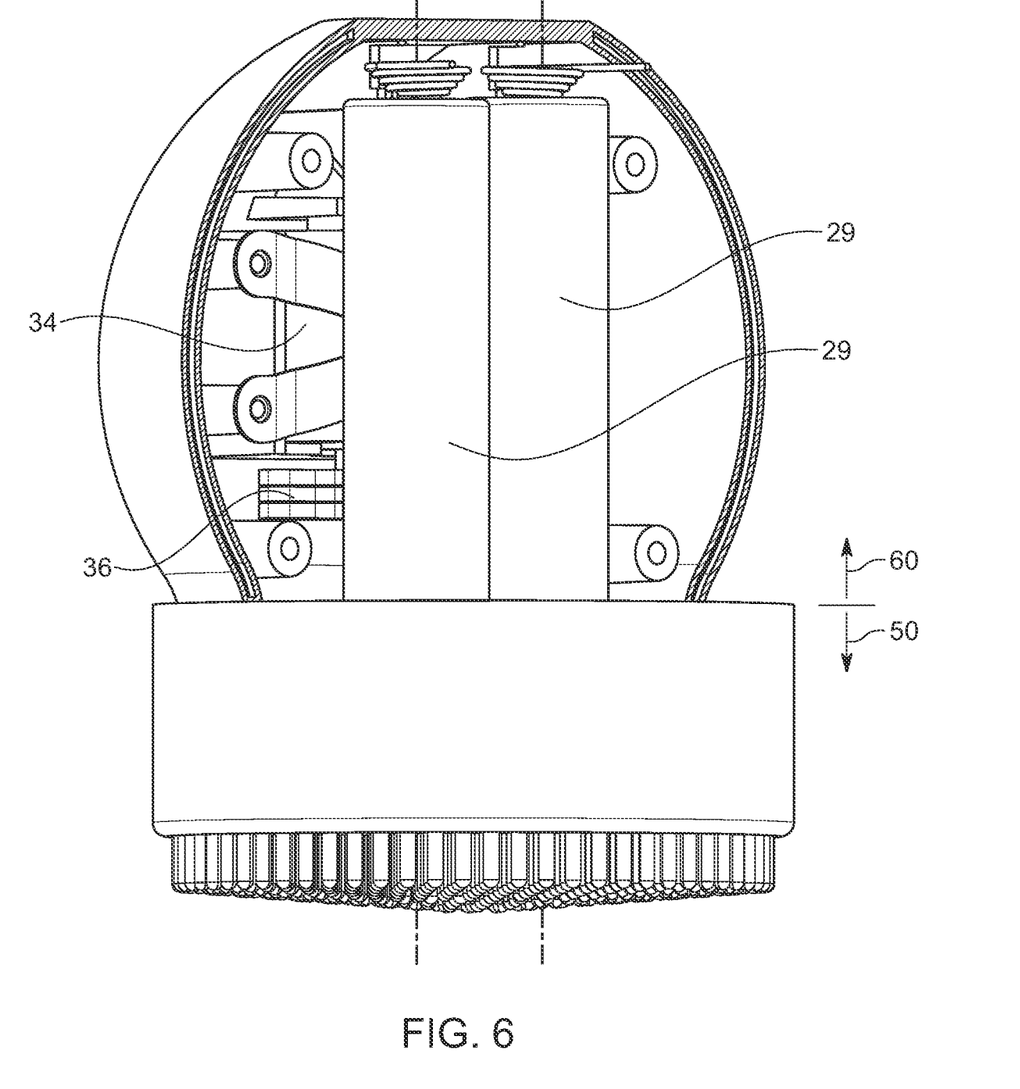
FIG. 6 illustrates a second cutaway view of the skin therapy device.

Referring to FIGS. 5 and 6, a first cutaway view and a second cutaway view the skin therapy device are shown.

The skin therapy device 1 is divided into the body 10 and the base 50. The body 10 includes a circuit board 28 with power button 32, mounted to a battery case 30.

Within the battery case 30 are batteries 29. The batteries are shown as single-use AAA batteries, but any type of battery power is anticipated. For example, lithium-ion batteries, nickel-metal hydride batteries, and so forth.

The motor 34 with unbalanced weight 36 is also shown, serving as a source of vibration. Alternative sources of vibration include linear resonant actuators.

Figure 7:
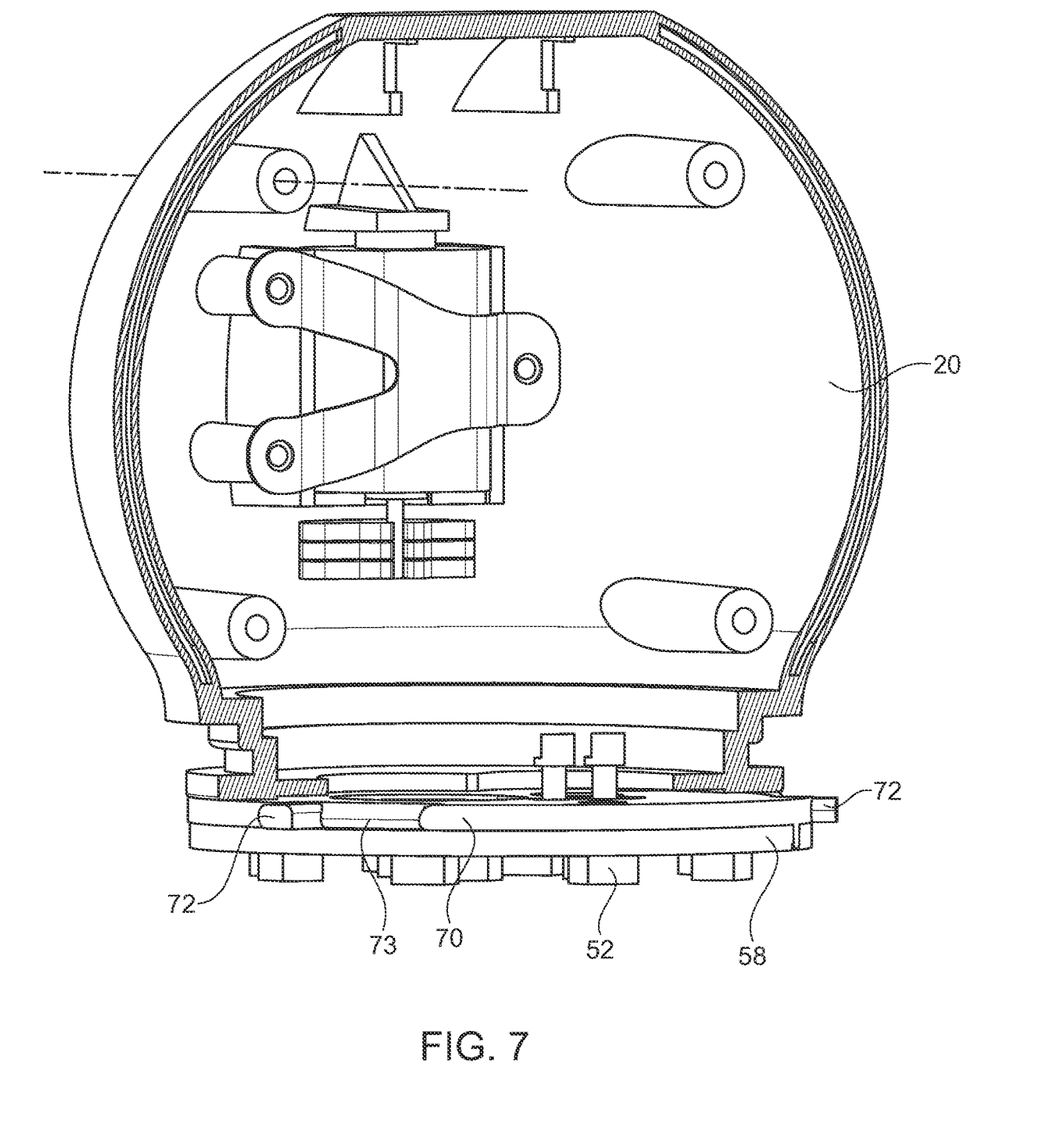
FIG. 7 illustrates a third cutaway view of the skin therapy device.
Figure 8:
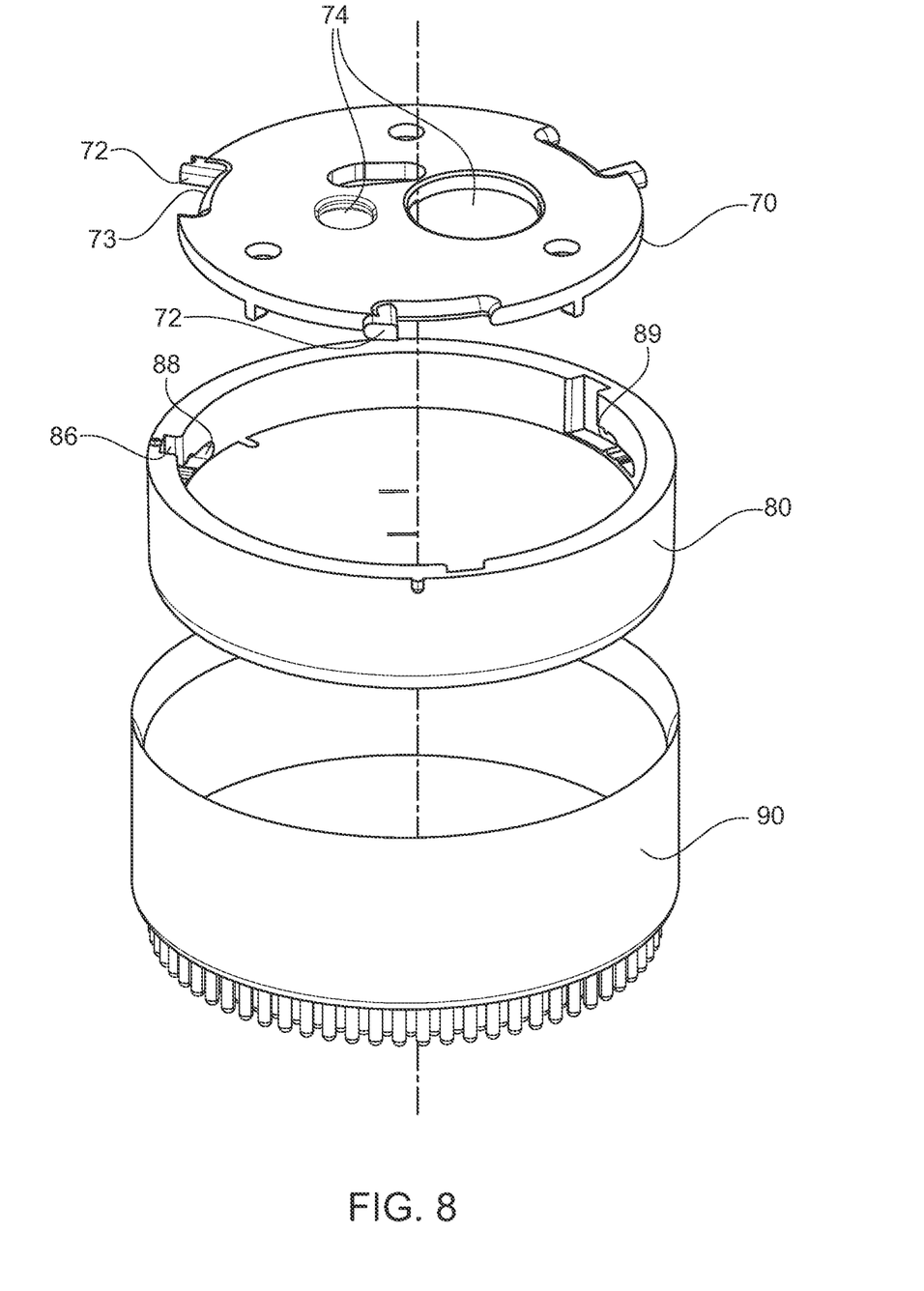
FIG. 8 illustrates an exploded view of the base and head, showing the locking features, of the skin therapy device.

Referring to FIGS. 7 and 8, a third cutaway view, and an exploded view of the base and head, showing the locking features, of the skin therapy device are shown.

The locking plate 70 includes two or more plate tabs 72 that interface with the protective cover 80 via the locking slot 86. The plate tabs rest in the first locking section 88 because the locking plate is inserted into the protective cover 80 before the protective cover 80 is attached to the inner shell 20.

The locking slot 86 further include a second locking section 89 that interfaces with the shell tabs 24 (see FIGS. 8 and 9) of the inner shell 20.

The shell tabs 24 nest within the plate gap 73 of the locking plate 70.

Figure 9:
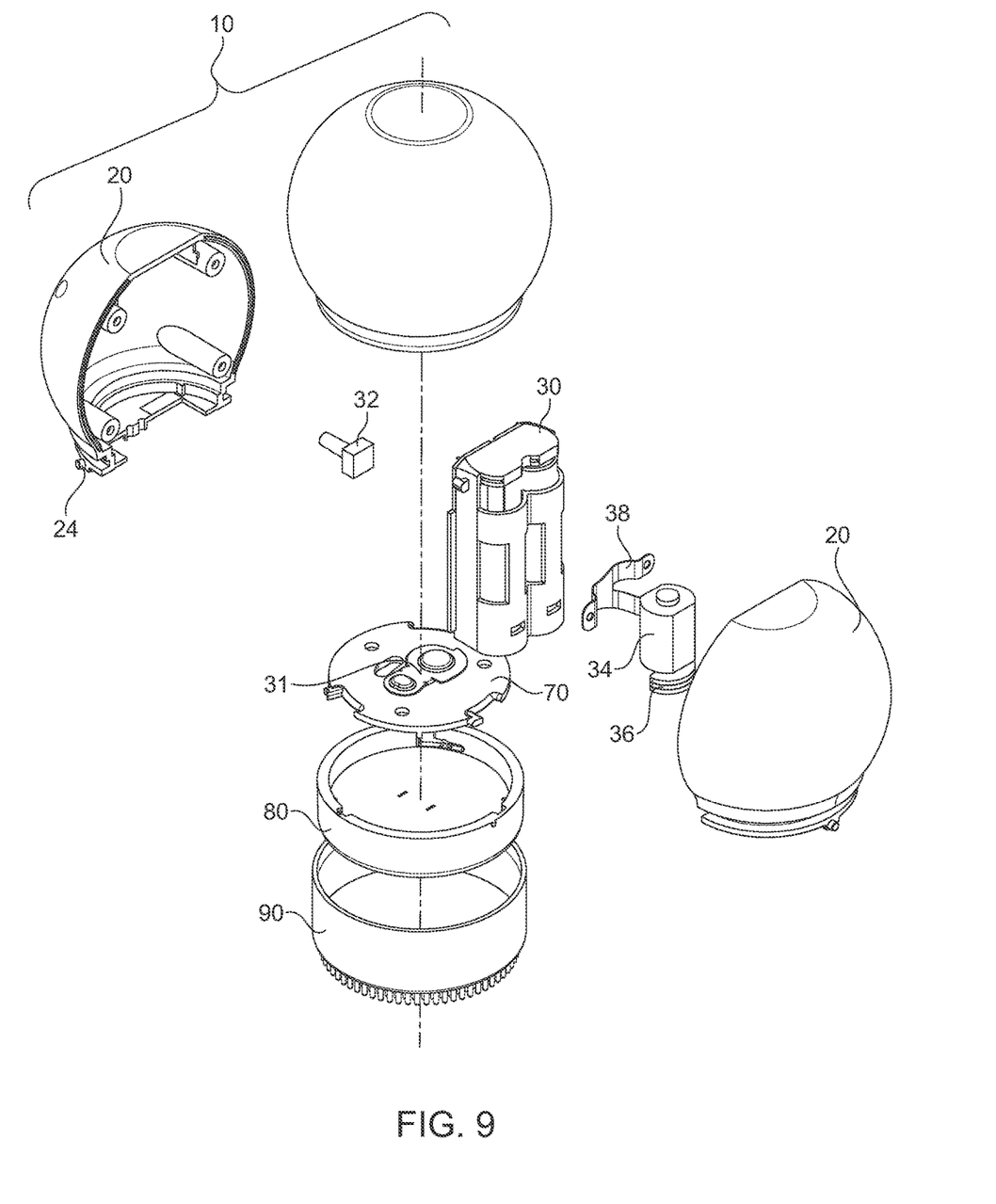
FIG. 9 illustrates an exploded view showing all parts of the skin therapy device.

The locking plate further includes battery through-holes 74 for supporting the battery jumper plate 31 (see FIG. 9).

Also shown is the silicone head 90 with cleansing head 92.

Figure 10:
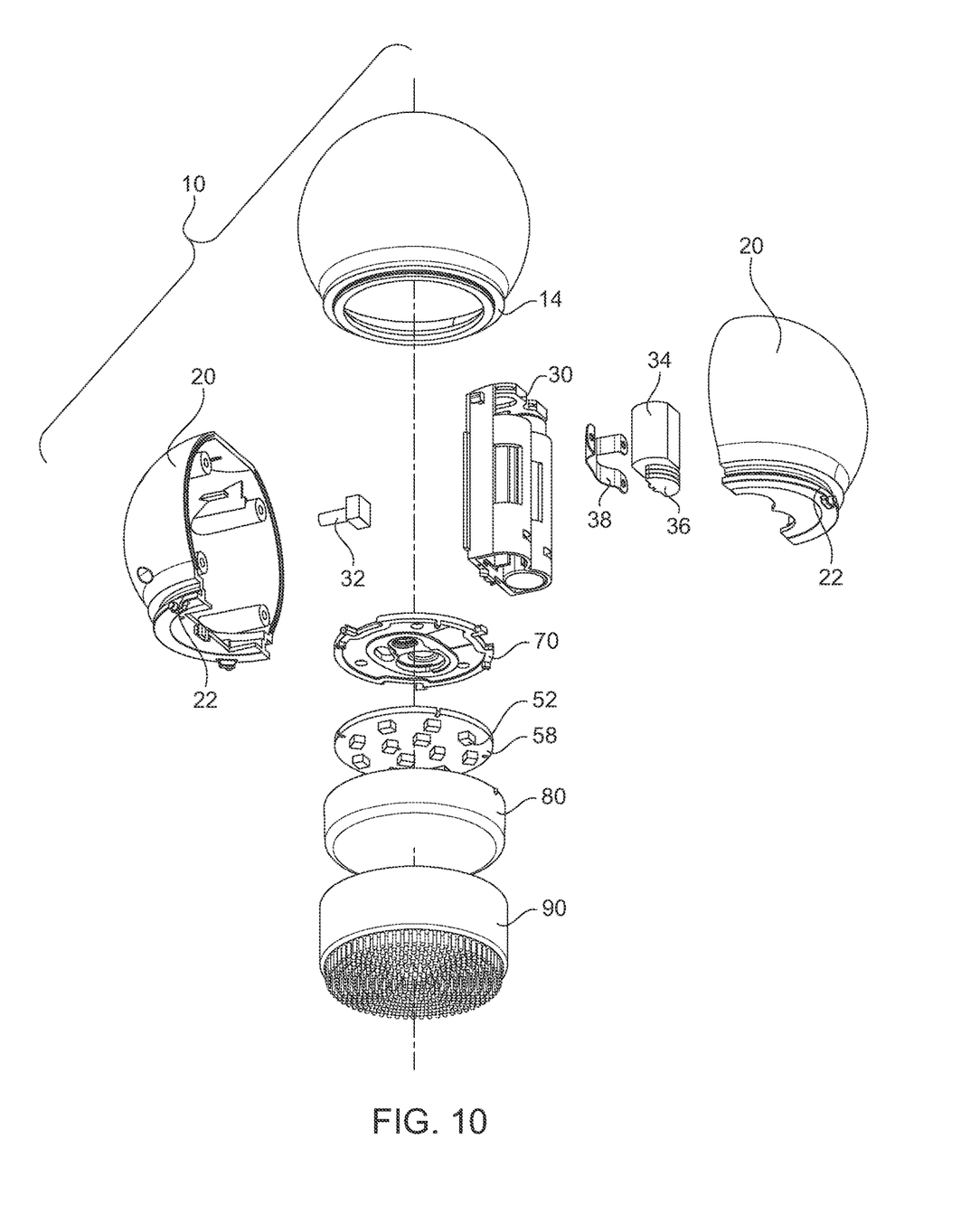
FIG. 10 illustrates a second exploded view showing all parts of the skin therapy device.

Referring to FIGS. 9 and 10, a first and second exploded view showing all parts of the skin therapy device is shown.

The skin therapy device 1 includes body 10 formed from an inner shell 20 with outer skin 12, the inner shell 20 including a locking ledge 22 to attach the inner shell 20 to the outer skin 12.

Within the body 10 is a battery case 30 with battery jumper plate 31 on the locking plate 70.

A power button 32 operates the skin therapy device 1.

Motor 34 with unbalanced weight 36 attaches to the inner shell 20 via motor bracket 38.

The locking plate 70 holds the LED circuit board 58 in place within the protective cover 80, the silicone head 90 fitting over the protective cover 80.

Figure 11:
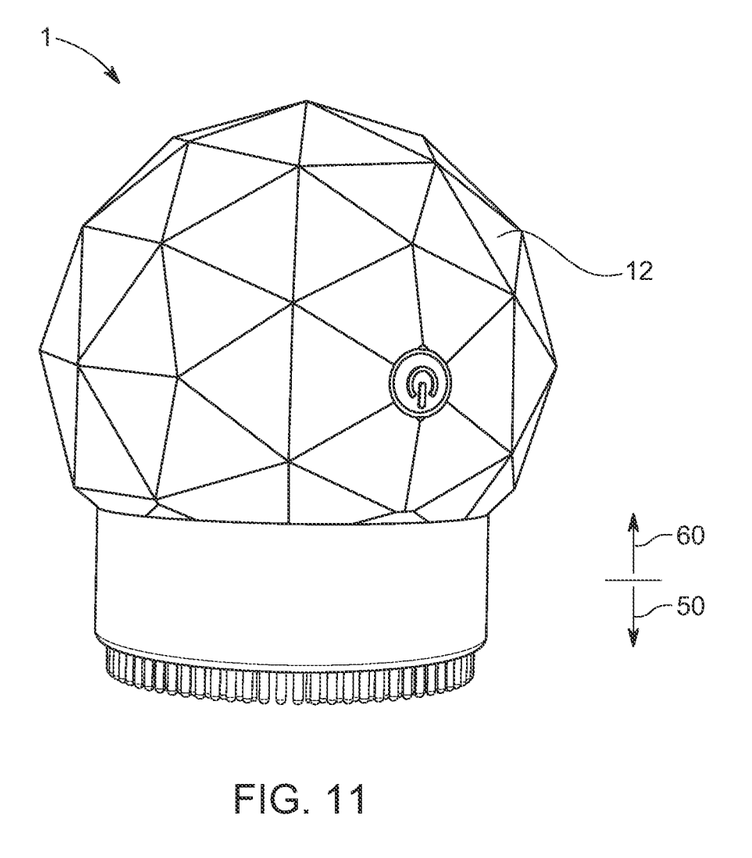
FIG. 11 illustrates a first alternative exterior shape for the skin therapy device.

Referring to FIG. 11, a first alternative exterior shape for the skin therapy device is shown.

The skin therapy device 1 includes a base 50 and body 10. The outer skin 12 is shown with a geometric shape.

Figure 12:
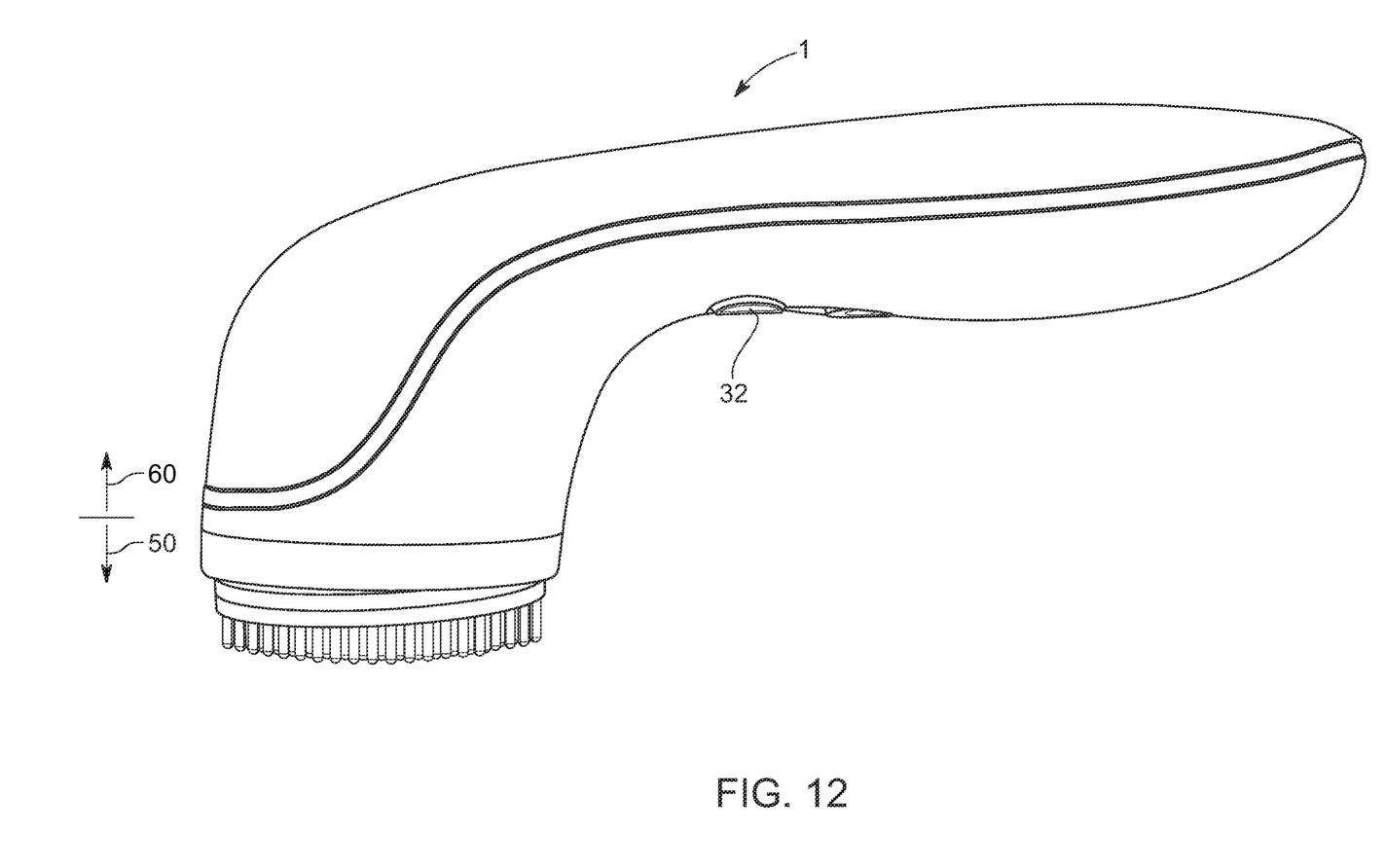
FIG. 12 illustrates a second alternative exterior shape for the skin therapy device.

Referring to FIG. 12, a second alternative exterior shape for the skin therapy device is shown.

The skin therapy device 1 includes a base 50 and body 10. The body 10 is elongated, creating a large grip for a user. The power button 32 is on the lower section of the grip, where a user's fingers will sit.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction, and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A skin therapy device that simultaneously provides mechanical and optical skin therapy to skin of a user, the skin therapy device comprising:
   a body;
   a protective cover;
   the protective cover affixed to the body;
   a silicone head;

the silicone head affixed to the protective cover;
one or more LEDs;
the one or more LEDs emitting light at a first wavelength;
the one or more LEDs physically shielded by the protective cover;
the one or more LEDs oriented to emit light through the protective cover, through the silicone head, and into the skin;
a vibration source;
the vibration source affixed to the body;
the vibration source causing vibration of the body, passing through the protective cover, through the silicone head, and finally to the skin;
a locking plate;
the locking plate mechanically connecting the body to the protective cover;
the protective cover includes a locking slot;
the locking slot includes a first locking section and a second locking section;
the locking plate includes a plate tab;
the plate tab interfacing with the first locking section;
the body includes a shell tab;
the shell tab interfacing with the second locking section;
whereby the locking plate removably joins the body to the protective cover and carries vibration of the body through to the protective cover, where the vibration passes to the silicone head; and
whereby the user powers up the skin therapy device to vibrate the silicone head, which vibrates against the skin, while the skin is further stimulated by the light at the first wavelength.

2. The skin therapy device of claim 1, wherein:
the one or more LEDs is a first LED set that emits light at the first wavelength, and a second LED set that emits light at a second wavelength.

3. The skin therapy device of claim 2, wherein:
the first wavelength is 415 nm; and
the second wavelength is 630 nm;
whereby combining the first wavelength and the second wavelength is effective in treating acne.

4. The skin therapy device of claim 1, wherein:
the one or more LEDs is a first LED set that emits light at the first wavelength, a second LED set that emits light at a second wavelength, a third LED set that emits light at a third wavelength, and a fourth LED set that emits light at a fourth wavelength.

5. The skin therapy device of claim 4, wherein:
the first wavelength is 605 nm; and
the second wavelength is 630 nm;
the third wavelength is 660 nm; and
the fourth wavelength is 880 nm;
whereby combining the first wavelength, the second wavelength, the third wavelength, and the fourth wavelength is effective in treating skin aging.

6. The skin therapy device of claim 1, wherein the vibration source is an electric motor with a shaft;
an unbalanced weight affixed to the shaft;
whereby rotation of the unbalanced weight causes the shaft to oscillate, creating vibration.

7. The skin therapy device of claim 1, wherein the silicone head is formed from a flexible material, allowing the silicone head to be stretched or rolled over the protective cover.

8. A skin therapy device for skin of a user, the skin therapy device comprising:
a body;
LEDs;
the LEDs emitting light at a first wavelength;
a protective cover surrounding the LEDs;
the protective cover transparent to light at the first wavelength;
the protective cover affixed to the body;
a flexible head;
the flexible head including protrusions;
the flexible head removably affixed to the protective cover;
the flexible head transparent to light at the first wavelength;
a vibration source;
the vibration source affixed to the body;
vibrations created by the vibration source passing through the body, through the protective cover, and into the flexible head;
a locking plate;
the locking plate mechanically connecting the body to the protective cover;
the protective cover includes a locking slot;
the locking slot includes a first locking section and a second locking section;
the locking plate includes a plate tab;
the plate tab interfacing with the first locking section;
the body includes a shell tab;
the shell tab interfacing with the second locking section;
whereby the locking plate removably joins the body to the protective cover and carries vibration of the body through to the protective cover, where the vibration passes to the flexible head; and
whereby the skin is simultaneously stimulated by the light at the first wavelength and vibrations from the vibration source, resulting in a therapeutic effect.

9. The skin therapy device of claim 8, wherein:
the LEDs further emit light at a second wavelength.

10. The skin therapy device of claim 9, wherein:
the first wavelength is 415 nm; and
the second wavelength is 630 nm;
whereby combining the first wavelength and the second wavelength is effective in treating acne.

11. The skin therapy device of claim 8, wherein:
the LEDs further emit light at a second wavelength, a third wavelength, and a fourth wavelength.

12. The skin therapy device of claim 11, wherein:
the first wavelength is 605 nm; and
the second wavelength is 630 nm;
the third wavelength is 660 nm; and
the fourth wavelength is 880 nm;
whereby combining the first wavelength, the second wavelength, the third wavelength, and the fourth wavelength is effective in treating skin aging.

13. The skin therapy device of claim 8, wherein the vibration source is an electric motor with a shaft;
an unbalanced weight affixed to the shaft;
whereby rotation of the unbalanced weight causes the shaft to oscillate, creating vibration.

14. The skin therapy device of claim 8, wherein the flexible head is formed from a flexible material, allowing the flexible head to be stretched or rolled, over the protective cover.

15. A skin therapy device for skin of a user, the skin therapy device comprising:
a body;
LEDs;

the LEDs emitting light at a first wavelength and a second wavelength;
a protective cover surrounding the LEDs;
  the protective cover transparent to light at the first wavelength;
  the protective cover affixed to the body;
a locking plate;
  the locking plate mechanically connecting the body to the protective cover;
  the protective cover including a locking slot;
    the locking slot including a first locking section and a second locking section;
  the locking plate including a plate tab;
    the plate tab interfacing with the first locking section;
  the body includes a shell tab;
    the shell tab interfacing with the second locking section;
a flexible head;
  the flexible head including protrusions;
  the flexible head removably affixed to the protective cover;
  the flexible head transparent to light at the first wavelength;
a motor with an unbalanced weight affixed to a shaft of the motor;
  rotation of the unbalanced weight causing the shaft to oscillate, creating vibration;
  the vibration passing through the body, through the protective cover, and into the flexible head;
whereby the skin is simultaneously stimulated by the light at the first wavelength and vibrations from the motor, resulting in a therapeutic effect.

* * * * *